US012630945B2

(12) United States Patent
Chen et al.

(10) Patent No.: US 12,630,945 B2
(45) Date of Patent: May 19, 2026

(54) METHOD FOR SERICIN REMOVAL

(71) Applicant: WENZHOU MUQING BIOTECHNOLOGY CO., LTD, Zhejiang (CN)

(72) Inventors: Shixuan Chen, Zhejiang (CN); Hua Xu, Zhejiang (CN); Hao Pan, Zhejiang (CN)

(73) Assignee: Wenzhou Muqing Biotechnology Co., Ltd, Wenzhou (CN)

( * ) Notice: Subject to any disclaimer, the term of this patent is extended or adjusted under 35 U.S.C. 154(b) by 463 days.

(21) Appl. No.: 18/018,973

(22) PCT Filed: Oct. 11, 2022

(86) PCT No.: PCT/CN2022/124485
§ 371 (c)(1),
(2) Date: Jan. 31, 2023

(87) PCT Pub. No.: WO2024/050915
PCT Pub. Date: Mar. 14, 2024

(65) Prior Publication Data
US 2024/0254173 A1 Aug. 1, 2024

(30) Foreign Application Priority Data

Sep. 9, 2022 (CN) .......................... 202211101562.6

(51) Int. Cl.
*D01C 3/02* (2006.01)
*C07K 14/435* (2006.01)

(52) U.S. Cl.
CPC .......... *D01C 3/02* (2013.01); *C07K 14/43586* (2013.01)

(58) Field of Classification Search
CPC ............... D01C 3/02; C07K 14/43586; D10B 2211/04; D04H 1/09; D06P 3/045;
(Continued)

(56) References Cited

U.S. PATENT DOCUMENTS 1,948,568 A * 2/1934 De R. Faber et al. . D06P 1/965
261/78.2
5,862,806 A * 1/1999 Cheung ............... A61L 27/3683
8/94.11

FOREIGN PATENT DOCUMENTS

CN 102605439 A 7/2012
CN 103613652 A 3/2014
(Continued)

OTHER PUBLICATIONS

Machine Translation of JP2002265498 (Sep. 18, 2002), 27 pages, attached as a pdf, Translated by EPO and Google on Mar. 18, 2025 (Year: 2025).*
Jiang et al., Expanded 3D Nanofiber Scaffolds: Cell Penetration, Neovascularization, and Host Response. Adv Healthc Mater. Dec. 2016;5(23):2993-3003. doi: 10.1002/adhm.201600808. Epub Oct. 6, 2016. PMID: 27709840; PMCID: PMC5143187 (Year: 2016).*
(Continued)

*Primary Examiner* — Randall L Beane
(74) *Attorney, Agent, or Firm* — MacMillan, Sobanski & Todd, LLC

(57) ABSTRACT
The present disclosure provides a method for sericin removal. Since sodium borohydride has a high hydrogen storage performance, a convenient hydrogen release, and relatively-stable chemical properties, the sodium borohydride in a sodium borohydride aqueous solution reacts with water slowly to release hydrogen. A large number of accumulated hydrogen bubbles pass through silk fibers, and produce an upward pulling force to the sericin on a fiber surface along the silk fibers under the action of inertial force and surface tension, thereby achieving the sericin removal at room temperature. Moreover, the method for sericin removal has a simple process, a complete sericin removal effect, and no damage to the structure of silk fibroin fibers, and can prepare the silk fibroin fibers with high flexibility and bright color.

9 Claims, 5 Drawing Sheets

(58) Field of Classification Search
CPC ...... D03D 15/233; D01B 7/06; D06N 3/0015;
Y10S 8/917
See application file for complete search history.

(56) References Cited

FOREIGN PATENT DOCUMENTS

| CN | 106319644 | A | * | 1/2017 | ............... D01C 3/02 |
|----|-----------|---|---|--------|--------------------------|
| CN | 106676642 | A |   | 5/2017 | |
| CN | 107385525 | A |   | 11/2017 | |
| CN | 109518299 | A |   | 3/2019 | |
| CN | 111058286 | A |   | 4/2020 | |
| CN | 111101207 | A |   | 5/2020 | |
| DE | 295944 | C |   | 12/1916 | |
| FR | 336280 | A |   | 3/1904 | |
| GB | 100029 | A |   | 5/1916 | |
| JP | 2002265498 | A | * | 9/2002 | |

OTHER PUBLICATIONS

Jiang et al., Expanding Two-Dimensional Electrospun Nanofiber Membranes in the Third Dimension by a Modified Gas-Foaming Technique. ACS Biomater Sci Eng. Oct. 12, 2015;1(10):991-1001. doi: 10.1021/acsbiomaterials.5b00238. Epub Aug. 27, 2015. PMID: 33429530 (Year: 2015).*

Wongpinyochit et al., Manufacture and Drug Delivery Applications of Silk Nanoparticles. J Vis Exp. Oct. 8, 2016;(116):54669. doi: 10.3791/54669. PMID: 27768078; PMCID: PMC5092179 (Year: 2016).*

Chinese First Office Action, dated Mar. 18, 2023, Application No. 202211101562.6.

PCT International Search Report, mailed May 16, 2023, Application No. PCT/CN2022/124485.

Feng et al., "Sodium Borohydride and the Production of New Energy Hydrogen," Beijing Metallurgical Industry Publishing House, (2018), 2.1-2.2.1.

* cited by examiner

METHOD FOR SERICIN REMOVAL

CROSS REFERENCE TO RELATED APPLICATION

The present application claims priority to the Chinese Patent Application No. 202211101562.6, filed with the China National Intellectual Property Administration (CNIPA) on Sep. 9, 2022, and entitled "METHOD FOR SERICIN REMOVAL", which is incorporated herein by reference in its entirety.

TECHNICAL FIELD

The present disclosure relates to the field of fiber materials, in particular to a method for sericin removal.

BACKGROUND

Silk is a natural fiber material, generally composed of about 70% of silk fibroin (SF) and about 25% of sericin, and 5% of impurities as a balance. With the development and utilization of new materials, the silk gradually shows excellent properties in the field of biomedical materials. Silk fibroin fiber can be used as a new medical material with unique biodegradability and desirable mechanical properties, which is widely used in drug release, artificial bone tissue scaffolds, wound dressings, artificial eardrums, and nerve conduits.

During preparation of silk fibroin fibers by sericin removal, it is particularly important to select appropriate sericin removal methods and parameters, which may directly affect the properties of silk fibroin. For example, during the sericin removal, the integrity and uniformity of sericin removal can directly affect the softness, smoothness, and gloss of silk fibroin after the sericin removal. At present, the sericin removal is conducted by alkalies, soaps, urea, organic acids, ionic liquids, high temperature and high pressure, ultrasonic wave, microwave, and enzymes. However, these methods generally have incomplete sericin removal, time-consuming and labor-intensive processes, and serious damages to the structure of silk fibroin fiber. Therefore, there is an urgent need to provide a method for sericin removal with a simple process and complete sericin removal and without destroying the structure of silk fibroin fiber.

SUMMARY

An objective of the present disclosure is to provide a method for sericin removal. The method for sericin removal has a simple process, a complete sericin removal effect, and no damage to the structure of silk fibroin fibers, and can prepare the silk fibroin fibers with high flexibility and bright color.

To achieve the above objective of the present disclosure, the present disclosure provides the following technical solutions.

The present disclosure provides a method for sericin removal, including the following steps:

conducting sericin removal by immersing a silkworm cocoon into a sodium borohydride aqueous solution, and washing and drying in sequence to obtain a silk fibroin fiber; where the sericin removal is conducted at room temperature for 1.5 h to 26 h.

Preferably, the silkworm cocoon is cut into slices prior to use.

Preferably, the sodium borohydride aqueous solution has a mass concentration of 0.2% to 5%.

Preferably, the sodium borohydride aqueous solution has a mass concentration of 0.3% to 4%.

Preferably, the silkworm cocoon and the sodium borohydride aqueous solution have a mass-to-volume ratio of 1 g:(25-50) mL.

Preferably, the silkworm cocoon and the sodium borohydride aqueous solution have a mass-to-volume ratio of 1 g:(30-40) mL.

Preferably, the sericin removal is conducted for 2 h to 25 h.

Preferably, the washing is conducted with distilled water 4 to 6 times.

Preferably, the washing is conducted 5 times.

Preferably, the silkworm cocoon and the distilled water have a mass-volume ratio of 1 g:(350-500) mL.

Preferably, the silkworm cocoon and the distilled water have a mass-volume ratio of 1 g:(370-450) mL.

Preferably, the drying is conducted by freeze-drying.

The present disclosure provides a method for sericin removal. Since sodium borohydride has a high hydrogen storage performance, a convenient hydrogen release, and relatively-stable chemical properties, the sodium borohydride in a sodium borohydride aqueous solution reacts with water slowly to release hydrogen. A large number of accumulated hydrogen bubbles pass through silk fibers, and produce an upward pulling force to the sericin on a fiber surface along the silk fibers under the action of inertial force and surface tension, thereby achieving the sericin removal at room temperature. In traditional methods, the sodium carbonate solution needs to be boiled. Such a high-temperature reaction may cause the long chain of silk fibroin to be decomposed into short peptide chains, easily destroying the structure of silk fibroin; meanwhile, the high-temperature working environment may lead to accidents such as burns. In the present disclosure, the method conducts sericin removal on silkworm cocoons at room temperature, which has mild reaction conditions, so as to realize low energy consumption and simplified process; and the large number of hydrogen bubbles accumulated by the slow reaction of sodium borohydride with water pass through the silk fibers to achieve sericin removal, thus avoiding damages to the structure of silk fibroin fiber. The silk fibroin fibers prepared by sericin removal with traditional sodium carbonate solution are yellow-brown. This is because the main component of silk fibroin fiber is proteins composed of high-molecular amino acids, and has hydrophilic groups such as hydroxyl, carboxyl and amino groups. High temperature is prone to thermal oxidation to denature silk fibroin and make silk fibroin fibers secrete grease, thus making the silk fibroin fibers yellow and brittle. In the method provided by the present disclosure, sodium borohydride is decomposed in the aqueous solution to generate air bubbles to play a role of physical sericin removal, so as to avoid damages to the silk fibroin structure to the greatest extent, and to maintain white and bright color. In the method, the hydrogen gas bubbles generated by sodium borohydride are used to produce an upward pulling force to the sericin on a fiber surface along the silk fibers under the action of inertial force and surface tension, which does not destroy the structure of prepared silk fibroin fibers, and can prepare the silk fibroin fibers with high flexibility. The results of the examples show that the method provided by the present disclosure can achieve a better sericin removal effect, with a sericin removal efficiency reaching 25% to 33%, showing relatively complete sericin removal.

DETAILED DESCRIPTION OF THE EMBODIMENTS

Figure 1:
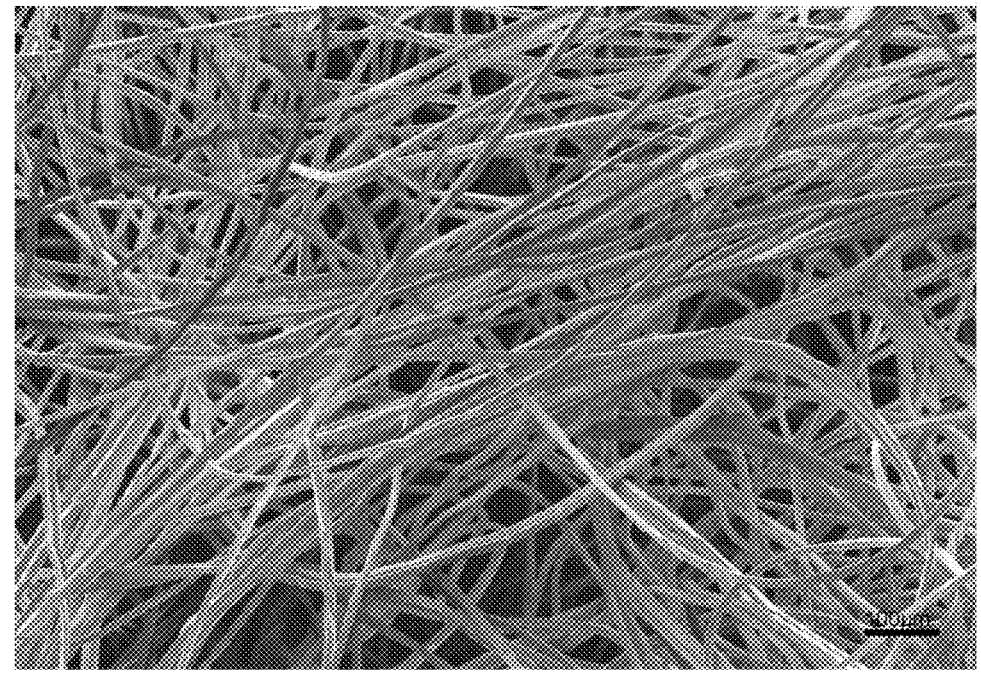
FIG. 1 shows an electron microscope scanning diagram of a silk fibroin fiber obtained in Comparative Example 10 of the present disclosure.
Figure 2:
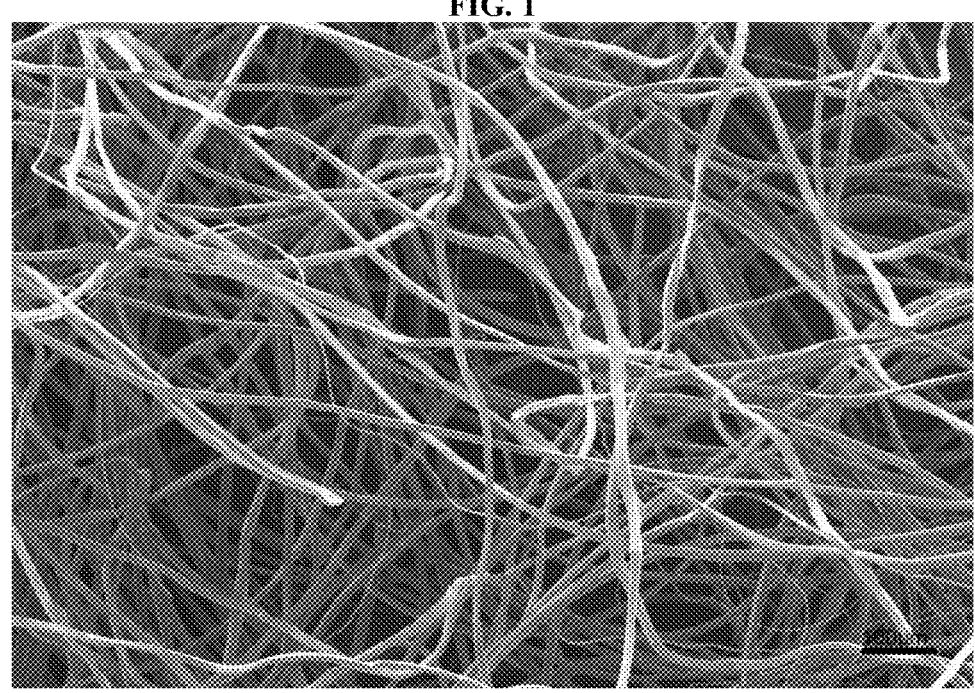
FIG. 2 shows an electron microscope scanning diagram of a silk fibroin fiber obtained in Example 3 of the present disclosure.
Figure 3:
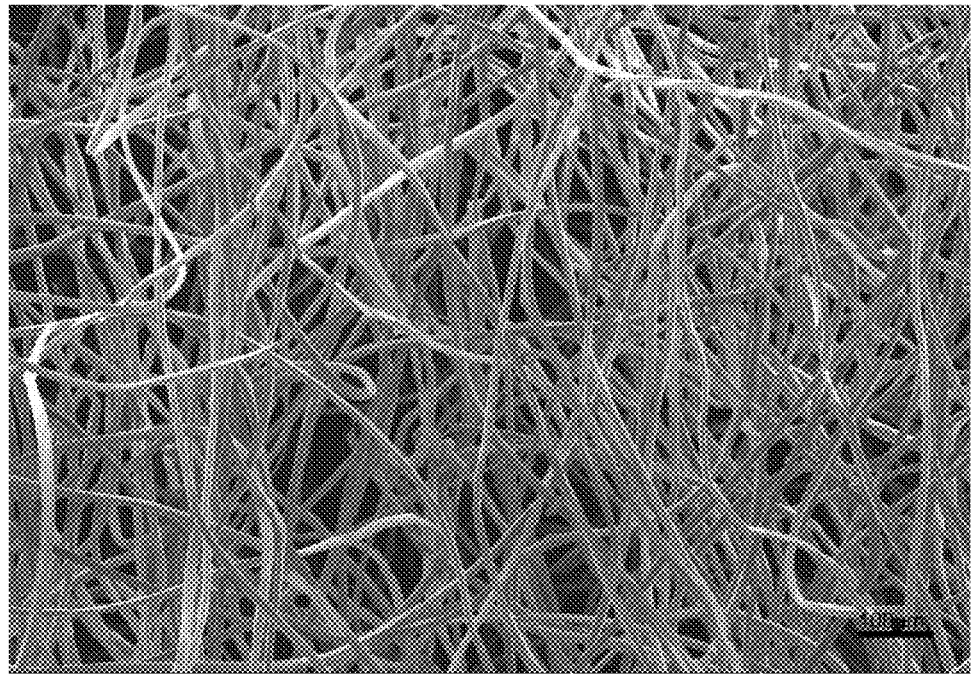
FIG. 3 shows an electron microscope scanning diagram of a silk fibroin fiber obtained in Example 10 of the present disclosure.
Figure 4:
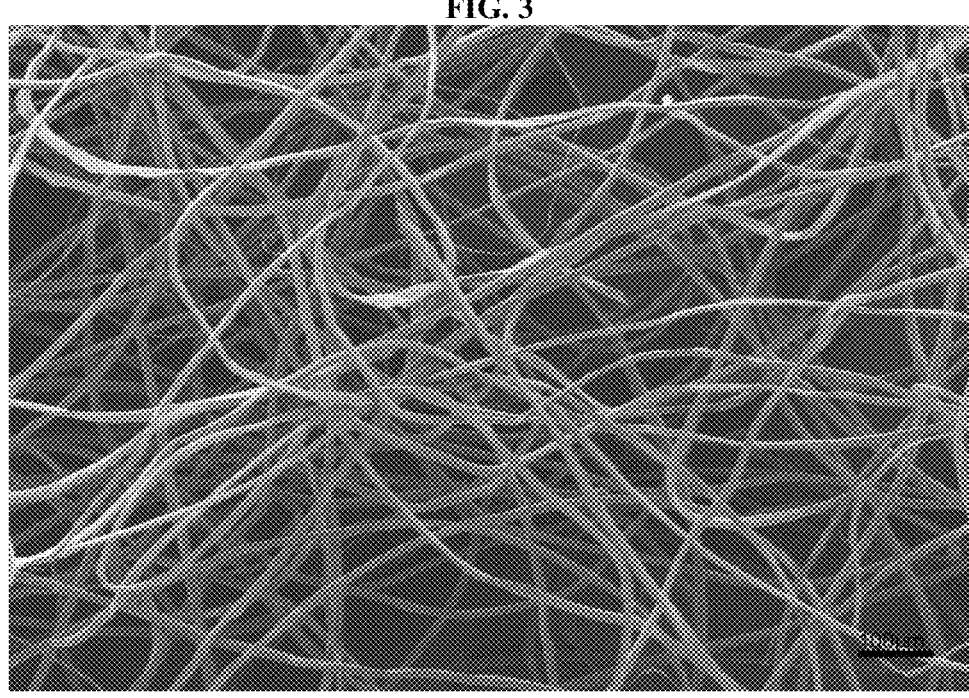
FIG. 4 shows an electron microscope scanning diagram of a silk fibroin fiber obtained in Example 17 of the present disclosure.

The present disclosure provides a method for sericin removal, including the following steps:

conducting sericin removal by immersing a silkworm cocoon into a sodium borohydride aqueous solution, and washing and drying in sequence to obtain a silk fibroin fiber; where the sericin removal is conducted at room temperature for 1.5 h to 26 h.

In the present disclosure, unless otherwise specified, all raw materials used are commercially available products conventional in the art.

In the present disclosure, the silkworm cocoon is preferably cut into slices prior to use.

In the present disclosure, the sodium borohydride aqueous solution has a mass concentration of preferably 0.2% to 5%, more preferably 0.3% to 4%. In an example, the sodium borohydride aqueous solution may have a mass concentration of 1%, 1.5%, 2%, 2.5%, or 3%. The mass concentration of the sodium borohydride aqueous solution is controlled within the above range to control a rate at which sodium borohydride and water form hydrogen, so as to achieve a better sericin removal effect at room temperature, thereby avoiding damages to the silk fibroin structure to the greatest extent and maintaining white and bright color.

In the present disclosure, the silkworm cocoon and the sodium borohydride aqueous solution have a mass-to-volume ratio of preferably 1 g:(25-50) mL, more preferably 1 g:(30-40) mL. The mass-volume ratio of the silkworm cocoon and the sodium borohydride aqueous solution is controlled within the above range to ensure that the silkworm cocoon is completely immersed in the sodium borohydride aqueous solution, which is conducive to the complete sericin removal to achieve a better sericin removal effect.

In the present disclosure, the sericin removal is conducted for preferably 2 h to 25 h. In an example, the sericin removal may be conducted for specifically 4 h, 6 h, 8 h, 12 h, 16 h, 20 h, or 24 h. Controlling the time of sericin removal within the above range is conducive to exploring the influence of sodium borohydride on the sericin removal of silkworm cocoon from the release of a small amount of hydrogen air bubbles to the release of hydrogen air bubbles to the maximum extent.

In the present disclosure, the washing is conducted with preferably distilled water. The washing is conducted preferably 4 to 8 times, more preferably 5 to 8 times. The number of times of washing is controlled within the above range to ensure that impurities on the surface of the silk fibroin fibers prepared after sericin removal are removed.

In the present disclosure, the silkworm cocoon and the distilled water have a mass-volume ratio of preferably 1 g:(350-500) mL, more preferably 1 g:(370-450) mL. Controlling the mass-volume ratio of silkworm cocoon and distilled water within the above range is conducive to removing impurities on the surface of the silk fibroin fibers prepared after sericin removal as much as possible.

In the present disclosure, the drying is conducted by preferably freeze-drying. The drying is conducted with a freeze dryer to avoid damages to the silk fibroin structure and maintain its white and bright color.

In the present disclosure, the method for sericin removal has simple operation and mild reaction conditions, and is suitable for large-scale production, and can prepare silk fibroin fibers with high flexibility and bright color.

The technical solutions of the present disclosure will be described below clearly and completely in conjunction with the examples of the present disclosure. Apparently, the described examples are only a part of, not all of, the examples of the present disclosure. All other embodiments obtained by those of ordinary skill in the art based on the embodiments of the present disclosure without creative efforts shall fall within the protection scope of the present disclosure.

Example 1

A method for sericin removal included:

A silkworm cocoon was cut into slices, and immersed into a sodium borohydride aqueous solution with a mass concentration of 1%, followed by sericin removal at room temperature for 6 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Example 1 was calculated by a weighing method, and a calculation formula was as follows:

$$\text{Sericin removal efficiency } (\%)=(A0-A1)/A0*100\%;$$
where

A0 was a dry weight of the silkworm cocoon before sericin removal, and A1 was a dry weight of the silkworm cocoon after sericin removal. The specific results were shown in Table 1.

Example 2

The sericin removal was conducted according to the method of Example 1, and the sericin removal efficiency was calculated by a same method, and the specific results were shown in Table 1: where this example differed from Example 1 in that the sericin removal was conducted for 8 h.

Example 3

The sericin removal was conducted according to the method of Example 1, and the sericin removal efficiency was calculated by a same method, and the specific results were shown in Table 1; where this example differed from Example 1 in that the sericin removal was conducted for 12 h.

Example 4

The sericin removal was conducted according to the method of Example 1, and the sericin removal efficiency was calculated by a same method, and the specific results were shown in Table 1; where this example differed from Example 1 in that the sericin removal was conducted for 16 h.

Example 5

The sericin removal was conducted according to the method of Example 1, and the sericin removal efficiency was calculated by a same method, and the specific results were shown in Table 1; where this example differed from Example 1 in that the sericin removal was conducted for 20 h.

Example 6

The sericin removal was conducted according to the method of Example 1, and the sericin removal efficiency was calculated by a same method, and the specific results were shown in Table 1; where this example differed from Example 1 in that the sericin removal was conducted for 24 h.

Example 7

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 1.5%, and the sericin removal was conducted for 4 h.

Example 8

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 1.5%.

Example 9

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 1.5%, and the sericin removal was conducted for 8 h.

Example 10

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 1.5%, and the sericin removal was conducted for 12 h.

Example 11

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 1.5%, and the sericin removal was conducted for 16 h.

Example 12

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 1.5%, and the sericin removal was conducted for 20 h.

Example 13

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 1.5%, and the sericin removal was conducted for 24 h.

Example 14

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2%, and the sericin removal was conducted for 4 h.

Example 15

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2%.

Example 16

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2%, and the sericin removal was conducted for 8 h.

Example 17

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2%, and the sericin removal was conducted for 12 h.

Example 18

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2%, and the sericin removal was conducted for 16 h.

Example 19

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2%, and the sericin removal was conducted for 20 h.

Example 20

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2%, and the sericin removal was conducted for 24 h.

Example 21

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2.5%, and the sericin removal was conducted for 4 h.

Example 22

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2.5%.

Example 23

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2.5%, and the sericin removal was conducted for 8 h.

Example 24

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2.5%, and the sericin removal was conducted for 12 h.

Example 25

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2.5%, and the sericin removal was conducted for 16 h.

Example 26

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2.5%, and the sericin removal was conducted for 20 h.

Example 27

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 2.5%, and the sericin removal was conducted for 24 h.

Example 28

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 3%, and the sericin removal was conducted for 4 h.

Example 29

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 3%.

Example 30

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 3%, and the sericin removal was conducted for 8 h.

Example 31

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 3%, and the sericin removal was conducted for 12 h.

Example 32

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 3%, and the sericin removal was conducted for 16 h.

Example 33

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 3%, and the sericin removal was conducted for 20 h.

Example 34

The sericin removal was conducted according to the method of Example 1, and the sericin removal efficiency was calculated by a same method, and the specific results were shown in Table 1; where this example differed from Example 1 in that the sodium borohydride aqueous solution had a mass concentration of 3%, and the sericin removal was conducted for 24 h.

Comparative Example 1

A silkworm cocoon was cut into slices, and immersed into a sodium borohydride aqueous solution with a mass concentration of 0.3%, followed by sericin removal at room temperature for 2 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 1 was calculated by a weighing method, and a calculation formula was as follows:

$$\text{Sericin removal efficiency } (\%) = (A0 - A1)/A0*100\%;$$
$$\text{where}$$

A0 was a dry weight of the silkworm cocoon before sericin removal, and A1 was a dry weight of the silkworm cocoon after sericin removal. The specific results were shown in Table 1.

Comparative Example 2

A silkworm cocoon was cut into slices, and immersed into a sodium borohydride aqueous solution with a mass concentration of 0.3%, followed by sericin removal at room temperature for 4 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 2 was calculated by a weighing method, and a calculation formula was as follows:

$$\text{Sericin removal efficiency } (\%) = (A0 - A1)/A0*100\%;$$
$$\text{where}$$

A0 was a dry weight of the silkworm cocoon before sericin removal, and A1 was a dry weight of the silkworm cocoon after sericin removal. The specific results were shown in Table 1.

Comparative Example 3

A silkworm cocoon was cut into slices, and immersed into a sodium borohydride aqueous solution with a mass concentration of 0.3%, followed by sericin removal at room temperature for 6 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 3 was calculated by a weighing method, and a calculation formula was as follows:

$$\text{Sericin removal efficiency } (\%) = (A0 - A1)/A0*100\%;$$
$$\text{where}$$

A0 was a dry weight of the silkworm cocoon before sericin removal, and A1 was a dry weight of the silkworm cocoon after sericin removal. The specific results were shown in Table 1.

Comparative Example 4

A silkworm cocoon was cut into slices, and immersed into a sodium borohydride aqueous solution with a mass concentration of 0.3%, followed by sericin removal at room temperature for 8 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 4 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 5

A silkworm cocoon was cut into slices, and immersed into a sodium borohydride aqueous solution with a mass concentration of 0.3%, followed by sericin removal at room temperature for 12 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 5 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 6

A silkworm cocoon was cut into slices, and immersed into a sodium borohydride aqueous solution with a mass concentration of 0.5%, followed by sericin removal at room temperature for 2 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 6 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 7

A silkworm cocoon was cut into slices, and immersed into a sodium borohydride aqueous solution with a mass concentration of 0.5%, followed by sericin removal at room temperature for 4 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 7 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 8

A silkworm cocoon was cut into slices, and immersed into a sodium borohydride aqueous solution with a mass concentration of 0.5%, followed by sericin removal at room temperature for 6 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 8 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 9

A silkworm cocoon was cut into slices, and immersed into a sodium borohydride aqueous solution with a mass concentration of 0.5%, followed by sericin removal at room temperature for 8 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 9 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 10

A silkworm cocoon was cut into slices, and immersed into a sodium borohydride aqueous solution with a mass concentration of 0.5%, followed by sericin removal at room temperature for 12 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 10 was calculated by a weighing method, and a calculation formula was as follows:

$$\text{Sericin removal efficiency (\%)} = (A0-A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 11

A silkworm cocoon was cut into slices, and immersed into a sodium borohydride aqueous solution with a mass concentration of 0.7%, followed by sericin removal at room temperature for 2 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 11 was calculated by a weighing method, and a calculation formula was as follows:

$$\text{Sericin removal efficiency (\%)} = (A0-A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 12

A silkworm cocoon was cut into slices, and immersed into a sodium borohydride aqueous solution with a mass concentration of 0.7%, followed by sericin removal at room temperature for 4 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 12 was calculated by a weighing method, and a calculation formula was as follows:

$$\text{Sericin removal efficiency (\%)} = (A0-A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 13

A silkworm cocoon was cut into slices, and immersed into a sodium borohydride aqueous solution with a mass concentration of 0.7%, followed by sericin removal at room temperature for 6 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 13 was calculated by a weighing method, and a calculation formula was as follows:

$$\text{Sericin removal efficiency (\%)} = (A0-A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 14

A silkworm cocoon was cut into slices, and immersed into a sodium borohydride aqueous solution with a mass concentration of 0.7%, followed by sericin removal at room temperature for 8 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 14 was calculated by a weighing method, and a calculation formula was as follows:

$$\text{Sericin removal efficiency (\%)} = (A0-A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 15

A silkworm cocoon was cut into slices, and immersed into a sodium borohydride aqueous solution with a mass concentration of 0.7%, followed by sericin removal at room temperature for 12 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 15 was calculated by a weighing method, and a calculation formula was as follows:

$$\text{Sericin removal efficiency (\%)} = (A0 - A1)/A0 * 100\%;$$
where

A0 was a dry weight of the silkworm cocoon before sericin removal, and A1 was a dry weight of the silkworm cocoon after sericin removal. The specific results were shown in Table 1.

Comparative Example 16

A silkworm cocoon was cut into slices, and immersed into a sodium borohydride aqueous solution with a mass concentration of 0.9%, followed by sericin removal at room temperature for 2 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 16 was calculated by a weighing method, and a calculation formula was as follows:

$$\text{Sericin removal efficiency (\%)} = (A0 - A1)/A0 * 100\%;$$
where

A0 was a dry weight of the silkworm cocoon before sericin removal, and A1 was a dry weight of the silkworm cocoon after sericin removal. The specific results were shown in Table 1.

Comparative Example 17

A silkworm cocoon was cut into slices, and immersed into a sodium borohydride aqueous solution with a mass concentration of 0.9%, followed by sericin removal at room temperature for 4 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 17 was calculated by a weighing method, and a calculation formula was as follows:

$$\text{Sericin removal efficiency (\%)} = (A0 - A1)/A0 * 100\%;$$
where

A0 was a dry weight of the silkworm cocoon before sericin removal, and A1 was a dry weight of the silkworm cocoon after sericin removal. The specific results were shown in Table 1.

Comparative Example 18

A silkworm cocoon was cut into slices, and immersed into a sodium borohydride aqueous solution with a mass concentration of 0.9%, followed by sericin removal at room temperature for 6 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 18 was calculated by a weighing method, and a calculation formula was as follows:

$$\text{Sericin removal efficiency (\%)} = (A0 - A1)/A0 * 100\%;$$
where

A0 was a dry weight of the silkworm cocoon before sericin removal, and A1 was a dry weight of the silkworm cocoon after sericin removal. The specific results were shown in Table 1.

Comparative Example 19

A silkworm cocoon was cut into slices, and immersed into a sodium borohydride aqueous solution with a mass concentration of 0.9%, followed by sericin removal at room temperature for 8 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 19 was calculated by a weighing method, and a calculation formula was as follows:

$$\text{Sericin removal efficiency (\%)} = (A0 - A1)/A0 * 100\%;$$
where

A0 was a dry weight of the silkworm cocoon before sericin removal, and A1 was a dry weight of the silkworm cocoon after sericin removal. The specific results were shown in Table 1.

Comparative Example 20

A silkworm cocoon was cut into slices, and immersed into a sodium borohydride aqueous solution with a mass concentration of 0.9%, followed by sericin removal at room temperature for 12 h: a product obtained by the sericin removal was ultrasonically washed with distilled water 5 times, and then dried in a freeze dryer to obtain a silk fibroin fiber.

The silkworm cocoon and the sodium borohydride aqueous solution had a mass-to-volume ratio of 1 g:35 mL.

The silkworm cocoon and the distilled water had a mass-volume ratio of 1 g:350 mL.

A sericin removal efficiency of Comparative Example 20 was calculated by a weighing method, and a calculation formula was as follows:

$$\text{Sericin removal efficiency (\%)} = (A0 - A1)/A0 * 100\%;$$
where

A0 was a dry weight of the silkworm cocoon before sericin removal, and A1 was a dry weight of the silkworm cocoon after sericin removal. The specific results were shown in Table 1.

Comparative Example 21

A silkworm cocoon was cut into slices, and immersed into a sodium carbonate aqueous solution with a mass concentration of 0.5%, followed by conducting sericin removal at 100° C. for 1 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 21 was calculated by a weighing method, and a calculation formula was as follows:

Sericin removal efficiency (%)=(A0−A1)/A0*100%; where

A0 was a dry weight of the silkworm cocoon before sericin removal, and A1 was a dry weight of the silkworm cocoon after sericin removal. The specific results were shown in Table 1.

Comparative Example 22

A silkworm cocoon was cut into slices, and immersed into a sodium carbonate aqueous solution with a mass concentration of 1%, followed by conducting sericin removal at 100° C. for 1 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 22 was calculated by a weighing method, and a calculation formula was as follows:

Sericin removal efficiency (%)=(A0−A1)/A0*100%; where

A0 was a dry weight of the silkworm cocoon before sericin removal, and A1 was a dry weight of the silkworm cocoon after sericin removal. The specific results were shown in Table 1.

Comparative Example 23

A silkworm cocoon was cut into slices, and immersed into a sodium carbonate aqueous solution with a mass concentration of 1.5%, followed by conducting sericin removal at 100° C. for 1 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Example 1 was calculated by a weighing method, and a calculation formula was as follows:

Sericin removal efficiency (%)=(A0−A1)/A0*100%; where

A0 was a dry weight of the silkworm cocoon before sericin removal, and A1 was a dry weight of the silkworm cocoon after sericin removal. The specific results were shown in Table 1.

Comparative Example 24

A silkworm cocoon was cut into slices, and immersed into a sodium carbonate aqueous solution with a mass concentration of 2%, followed by conducting sericin removal at 100° C. for 1 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 24 was calculated by a weighing method, and a calculation formula was as follows:

Sericin removal efficiency (%)=(A0−A1)/A0*100%; where

A0 was a dry weight of the silkworm cocoon before sericin removal, and A1 was a dry weight of the silkworm cocoon after sericin removal. The specific results were shown in Table 1.

Comparative Example 25

A silkworm cocoon was cut into slices, and immersed into a sodium carbonate aqueous solution with a mass concentration of 0.5%, followed by conducting sericin removal at 100° C. for 1.5 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 25 was calculated by a weighing method, and a calculation formula was as follows:

Sericin removal efficiency (%)=(A0−A1)/A0*100%; where

A0 was a dry weight of the silkworm cocoon before sericin removal, and A1 was a dry weight of the silkworm cocoon after sericin removal. The specific results were shown in Table 1.

Comparative Example 26

A silkworm cocoon was cut into slices, and immersed into a sodium carbonate aqueous solution with a mass concentration of 1%, followed by conducting sericin removal at 100° C. for 1.5 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 26 was calculated by a weighing method, and a calculation formula was as follows:

Sericin removal efficiency (%)=(A0−A1)/A0*100%; where

A0 was a dry weight of the silkworm cocoon before sericin removal, and A1 was a dry weight of the silkworm cocoon after sericin removal. The specific results were shown in Table 1.

Comparative Example 27

A silkworm cocoon was cut into slices, and immersed into a sodium carbonate aqueous solution with a mass concentration of 1.5%, followed by conducting sericin removal at 100° C. for 1.5 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 27 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 28

A silkworm cocoon was cut into slices, and immersed into a sodium carbonate aqueous solution with a mass concentration of 2%, followed by conducting sericin removal at 100° C. for 1.5 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 28 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 29

A silkworm cocoon was cut into slices, and immersed into a sodium carbonate aqueous solution with a mass concentration of 0.3%, followed by sericin removal at room temperature for 2 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 29 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 30

A silkworm cocoon was cut into slices, and immersed into a sodium carbonate aqueous solution with a mass concentration of 0.3%, followed by sericin removal at room temperature for 4 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 30 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 31

A silkworm cocoon was cut into slices, and immersed into a sodium carbonate aqueous solution with a mass concentration of 0.3%, followed by sericin removal at room temperature for 6 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 31 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 32

A silkworm cocoon was cut into slices, and immersed into a sodium carbonate aqueous solution with a mass concentration of 0.3%, followed by sericin removal at room temperature for 8 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 32 was calculated by a weighing method, and a calculation formula was as follows:

$$\text{Sericin removal efficiency (\%)} = (A0 - A1)/A0*100\%;$$
where

A0 was a dry weight of the silkworm cocoon before sericin removal, and A1 was a dry weight of the silkworm cocoon after sericin removal. The specific results were shown in Table 1.

Comparative Example 33

A silkworm cocoon was cut into slices, and immersed into a sodium carbonate aqueous solution with a mass concentration of 0.3%, followed by sericin removal at room temperature for 12 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL.

A sericin removal efficiency of Comparative Example 33 was calculated by a weighing method, and a calculation formula was as follows:

Sericin removal efficiency (%)=$(A0-A1)/A0*100\%$; where

A0 was a dry weight of the silkworm cocoon before sericin removal, and A1 was a dry weight of the silkworm cocoon after sericin removal. The specific results were shown in Table 1.

Comparative Example 34

A silkworm cocoon was cut into slices, and immersed into a sodium carbonate aqueous solution with a mass concentration of 0.5%, followed by sericin removal at room temperature for 2 h: a product obtained by the sericin removal was ultrasonically washed with distilled water 5 times, and then dried in a freeze dryer to obtain a silk fibroin fiber.

The silkworm cocoon and the sodium carbonate aqueous solution had a mass-to-volume ratio of 1 g:35 mL.

The silkworm cocoon and the distilled water had a mass-volume ratio of 1 g:350 mL. A sericin removal efficiency of Comparative Example 34 was calculated by a weighing method, and a calculation formula was as follows:

Sericin removal efficiency (%)=$(A0-A1)/A0*100\%$; where

A0 was a dry weight of the silkworm cocoon before sericin removal, and A1 was a dry weight of the silkworm cocoon after sericin removal. The specific results were shown in Table 1.

The sericin removal efficiencies of Comparative Examples 1 to 34 were calculated by the same method as that in Example 1. The sericin removal efficiencies calculated in Examples 1 to 34 and Comparative Examples 1 to 34 were shown in Table 1.

TABLE 1

Sericin removal efficiencies in
Examples and Comparative Examples

| | Sericin removal efficiencies (%) |
|---|---|
| Examples | |
| 1 | 25.03 |
| 2 | 25.36 |
| 3 | 25.76 |
| 4 | 26.36 |
| 5 | 26.40 |
| 6 | 26.55 |
| 7 | 25.58 |

TABLE 1-continued

Sericin removal efficiencies in
Examples and Comparative Examples

| | Sericin removal efficiencies (%) |
|---|---|
| 8 | 27.86 |
| 9 | 28.10 |
| 10 | 28.22 |
| 11 | 28.40 |
| 12 | 28.70 |
| 13 | 28.75 |
| 14 | 27.33 |
| 15 | 28.8 |
| 16 | 28.7 |
| 17 | 29.04 |
| 18 | 27.86 |
| 19 | 29.78 |
| 20 | 30.04 |
| 21 | 30.05 |
| 22 | 31.02 |
| 23 | 32.39 |
| 24 | 32.04 |
| 25 | 32.33 |
| 26 | 32.88 |
| 27 | 33.26 |
| 28 | 33.54 |
| 29 | 33.75 |
| 30 | 33.83 |
| 31 | 32.2 |
| 32 | 32.4 |
| 33 | 32.11 |
| 34 | 33.01 |
| Comparative examples | |
| 1 | 3.35 |
| 2 | 3.99 |
| 3 | 9.55 |
| 4 | 11.72 |
| 5 | 9.67 |
| 6 | 7.33 |
| 7 | 12.82 |
| 8 | 15.85 |
| 9 | 16.39 |
| 10 | 16.52 |
| 11 | 8.9 |
| 12 | 14.26 |
| 13 | 16.32 |
| 14 | 17.58 |
| 15 | 18.95 |
| 16 | 16.90 |
| 17 | 19.05 |
| 18 | 20.96 |
| 19 | 21.19 |
| 20 | 22.08 |
| 21 | 26.31 |
| 22 | 29.46 |
| 23 | 33.57 |
| 24 | 35.42 |
| 25 | 31.42 |
| 26 | 36.78 |
| 27 | 40.7 |
| 28 | 44.17 |
| 29 | — |
| 30 | — |
| 31 | — |
| 32 | — |
| 33 | — |
| 34 | — |

In the table, the values in "−" each were less than 1, which could be regarded as negative control.

The silk fibroin fibers obtained in Comparative Example 10, Example 3, Example 10, and Example 17 were scanned by electron microscopy to obtain electron microscope scanning diagrams, as shown in FIG. 1, FIG. 2, FIG. 3, and FIG. 4. After comparing FIG. 1, FIG. 2, FIG. 3, and FIG. 4, it was seen that the sericin on the surface of the silk fibroin fiber obtained in Comparative Example 10 was not completely removed after 12 h of sericin removal using a 0.5% sodium borohydride aqueous solution. However, in Example 3, Example 10, and Example 17, 1%, 1.5%, and 2% sodium borohydride aqueous solutions were used, respectively, to achieve a better sericin removal effect, showing relatively thorough sericin removal.

Figure 5:
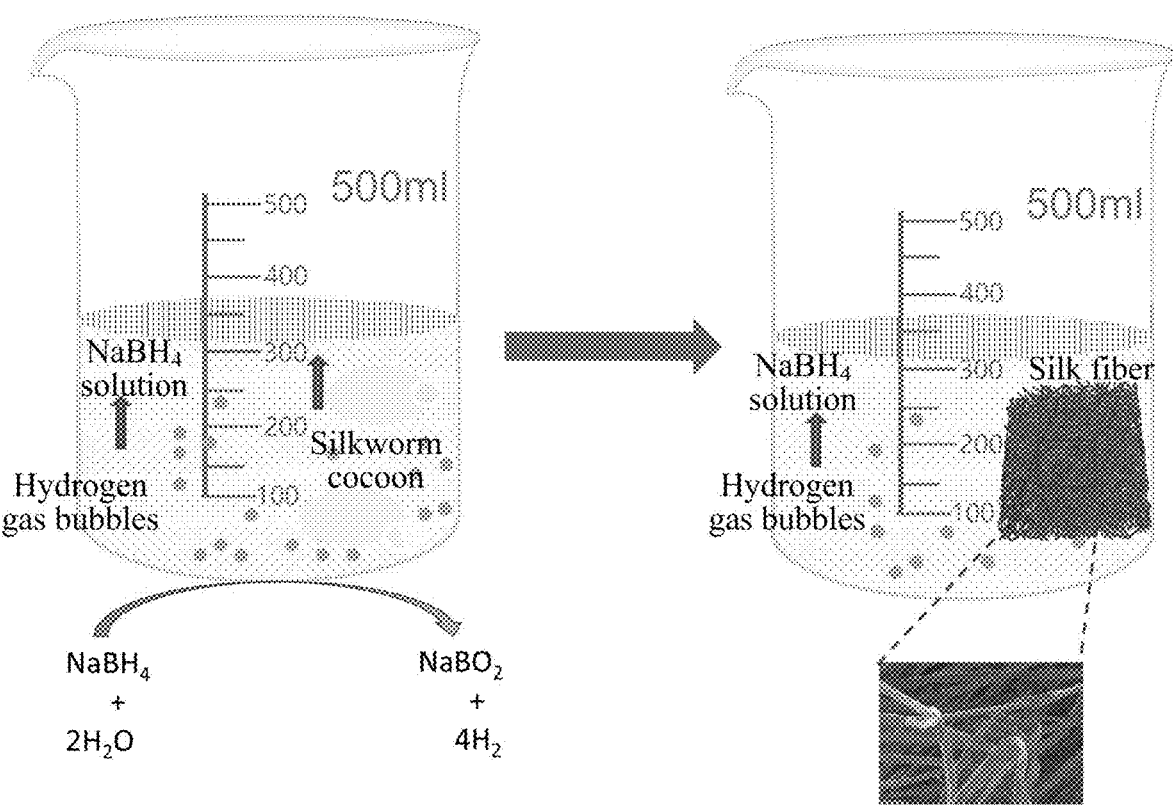
FIG. 5 shows a schematic diagram of a mechanism of the method for sericin removal provided by the present disclosure.

In the present disclosure, the mechanism of the method for sericin removal was shown in FIG. 5. The sodium borohydride in a sodium borohydride aqueous solution reacted with water slowly to release hydrogen. A large number of accumulated hydrogen bubbles passed through silk fibers, and produced an upward pulling force to the sericin on a fiber surface along the silk fibers under the action of inertial force and surface tension, thereby achieving the sericin removal at room temperature.

Figure 6:
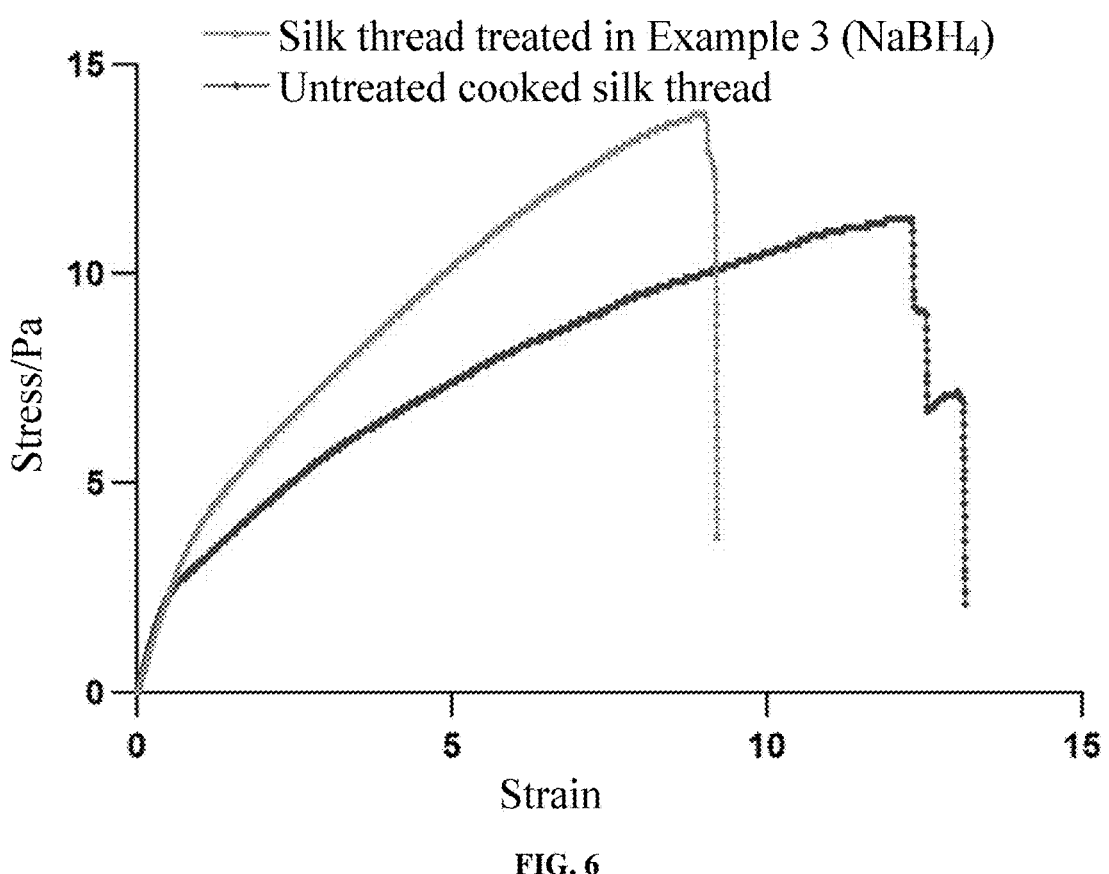
FIG. 6 shows stress-strain curves of a silk thread obtained in Example 3 of the present disclosure and an untreated cooked silk thread.

Tensile Test:

The raw silk threads and cooked silk threads were purchased in the market. The raw silk threads were treated according to the experimental method of Example 3 to obtain a silk thread treated by Example 3 (NaBH$_4$). The untreated cooked silk threads and the silk threads treated in Example 3 were cut into 5-cm thin threads separately, and both ends of a thin thread were glued to a square card with a length of 1 cm with an AB glue. The treated samples each were subjected to a tensile test using a universal material machine to obtain a stress-strain curve, as shown in FIG. 6. It was seen from FIG. 6 that a strength of the silk threads obtained after sericin removal with the sodium borohydride aqueous solution in Example 3 was significantly higher than that of the untreated cooked silk threads.

Figure 7:
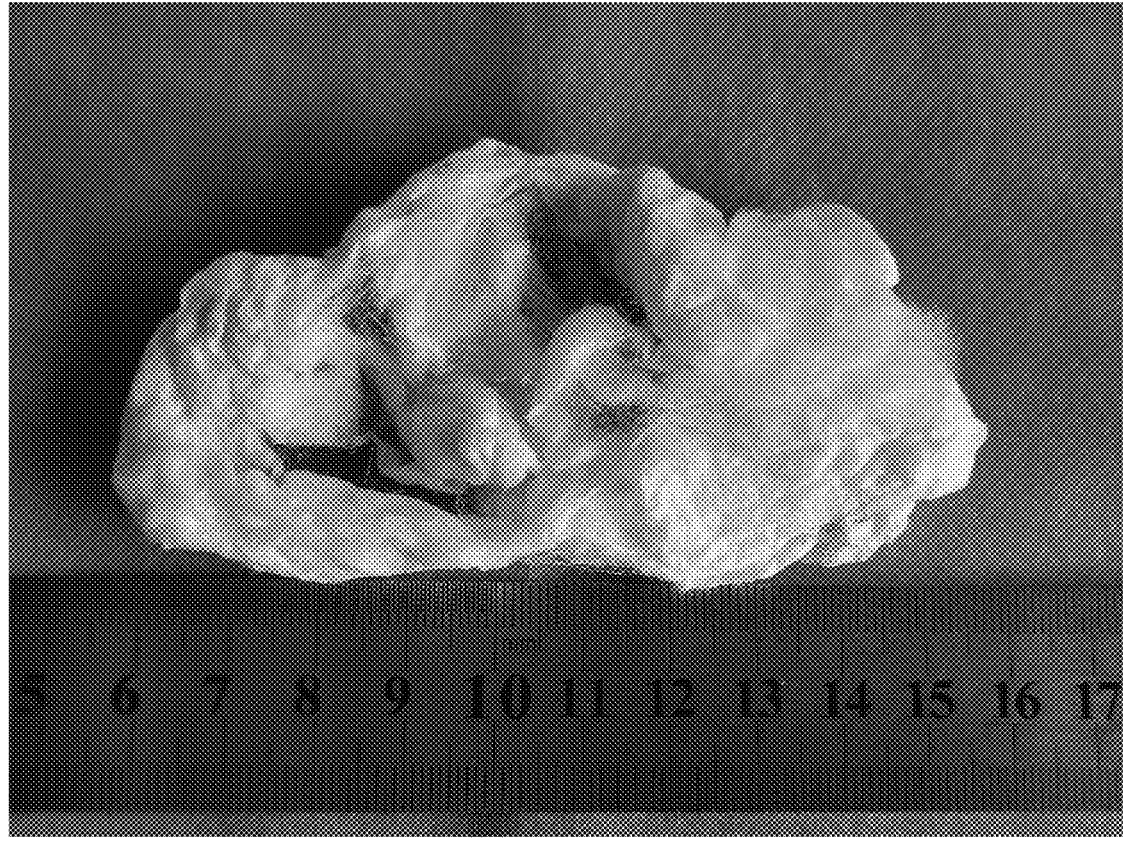
FIG. 7 shows a real picture of a silk fibroin fiber obtained in Comparative Example 21 of the present disclosure.
Figure 8:
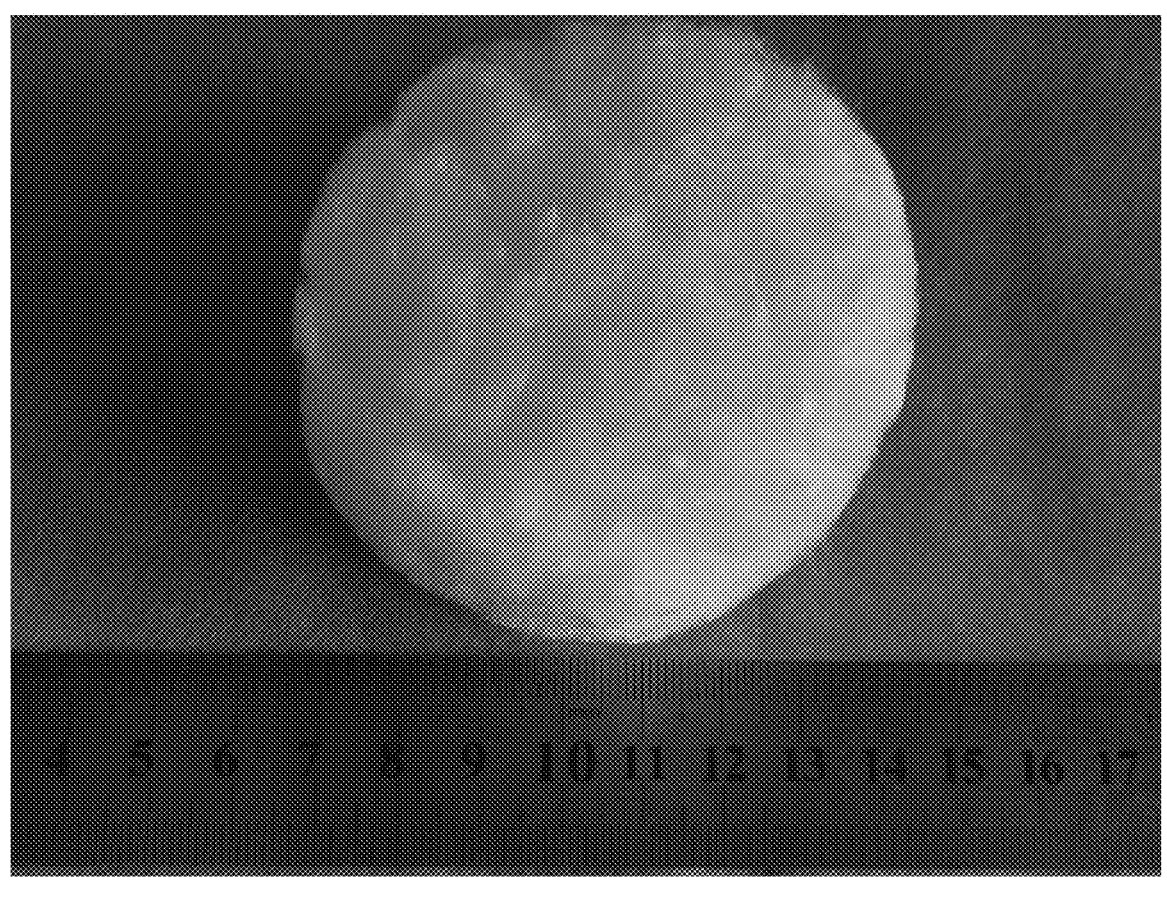
FIG. 8 shows a real picture of a silk fibroin fiber obtained in Example 3 of the present disclosure.

Through the methods of Comparative Example 21 and Example 3, the silk fibroin fibers obtained by sericin removal of silkworm cocoons were obtained, with real pictures shown in FIG. 7 and FIG. 8, respectively. It was seen from FIG. 7 and FIG. 8 that in Example 3, the bulkiness of the silk fibroin fiber sample after the sodium borohydride treatment reached the best effect, and the silk after sericin removal with sodium borohydride was white and bright.

In conclusion, the method provided by the present disclosure can achieve a better sericin removal effect, with a sericin removal efficiency reaching 25% to 33%, showing relatively complete sericin removal. Meanwhile, the material obtained by sericin removal with the sodium borohydride aqueous solution has excellent mechanical properties, white appearance, and desirable bulkiness.

The above description of examples is merely provided to help illustrate the method of the present disclosure and a core idea thereof. It should be noted that several improvements and modifications may be made by persons of ordinary skill in the art without departing from the principle of the present disclosure, and these improvements and modifications should also fall within the protection scope of the present disclosure. Various amendments to these embodiments are apparent to those of professional skill in the art, and the general principles defined herein may be implemented in other embodiments without departing from the spirit or scope of the present disclosure. Thus, the present disclosure is not limited to the examples shown herein but falls within the widest scope consistent with the principles and novel features disclosed herein.

What is claimed is:

1. A method for sericin removal, comprising the following steps:
   (a) making or obtaining a sodium borohydride aqueous solution having a mass concentration of 1% to 3% sodium borohydride;
   (b) conducting a sericin removal step to produce silk fibroin fibers, wherein the sericin removal step consists of immersing a silkworm cocoon into the sodium borohydride aqueous solution, at room temperature, for 6 h to 24 h; and
   (c) subsequently washing and drying, in sequence, the silk fibroin fibers produced by the sericin removal step.

2. The method according to claim 1, wherein the silkworm cocoon is cut into slices prior to use.

3. The method according to claim 1, wherein the sodium borohydride aqueous solution has a mass concentration of 1% to 2%.

4. The method according to claim 1, wherein the silkworm cocoon and the sodium borohydride aqueous solution have a mass-to-volume ratio of 1 g:(25-50) mL.

5. The method according to claim 4, wherein the silkworm cocoon and the sodium borohydride aqueous solution have a mass-to-volume ratio of 1 g:(30-40) mL.

6. The method according to claim 1, wherein the sericin removal step is conducted for 8 h to 16 h.

7. The method according to claim 1, wherein the washing is conducted with distilled water 4 to 6 times.

8. The method according to claim 7, wherein the washing is conducted 5 times.

9. The method according to claim 1, wherein the drying is conducted by freeze-drying.

* * * * *